(12) United States Patent
Gartside et al.

(10) Patent No.: US 6,420,619 B1
(45) Date of Patent: Jul. 16, 2002

(54) CRACKED GAS PROCESSING AND CONVERSION FOR PROPYLENE PRODUCTION

(76) Inventors: Robert J. Gartside, 167 Colonial Rd., Summit, NJ (US) 07901; Gary R. Gildert, 14507 Windy Ridge La., Houston, TX (US) 77062

( * ) Notice: Subject to any disclaimer, the term of this patent is extended or adjusted under 35 U.S.C. 154(b) by 0 days.

(21) Appl. No.: 09/769,871

(22) Filed: Jan. 25, 2001

(51) Int. Cl.[7] .............................. C07C 5/22; C07C 5/03; C07C 2/02; C07C 5/25; C10G 45/00
(52) U.S. Cl. ...................... 585/324; 585/253; 585/260; 585/518; 585/643; 585/664; 585/670; 208/57; 208/143; 208/145; 203/DIG. 6
(58) Field of Search .................. 208/57, 143, 145; 203/DIG. 6; 585/253, 260, 518, 324, 643, 664, 670

(56) References Cited

U.S. PATENT DOCUMENTS

| | | |
|---|---|---|
| 5,679,241 A | 10/1997 | Stanley et al. ............... 208/92 |
| 5,925,799 A | 7/1999 | Stanley et al. ............... 585/259 |
| 6,075,173 A | 6/2000 | Chodorge et al. ............ 585/324 |

OTHER PUBLICATIONS

Stanley, Stephen J. et al, "Alternate Routes to Enhanced Propylene Production", Petrotech, 98, Bahrain, Sep. 1998.

*Primary Examiner*—Walter D. Griffin
*Assistant Examiner*—Tam M. Nguyen
(74) *Attorney, Agent, or Firm*—Alix, Yale & Ristas, LLP

(57) ABSTRACT

The $C_3$ to $C_6$ cut from a cracking process containing propylene, butane, 1-butene, 2-butene and acetylenic and diene components including butadiene are preferentially converted to propylene. The cut is simultaneously fractionated and catalytically hydrogenated to hydrogenate the acetylenic and diene components. The fractionation and subsequent separation recovers a $C_4$ component comprising a mixture of isobutene, 1-butene and 2-butene. This $C_4$ component is then further simultaneously fractionated and catalytically hydrogenated and hydroisomerized to hydrogenate remaining butadiene, remove isobutene overhead and convert 1-butene to 2-butene leaving a bottoms of 2-butene. The 2-butene is then injected with ethylene and catalytically metathesized to form propylene.

9 Claims, 2 Drawing Sheets

CRACKED GAS PROCESSING AND CONVERSION FOR PROPYLENE PRODUCTION

BACKGROUND OF THE INVENTION

The present invention relates to the processing of a $C_3$ to $C_6$ hydrocarbon cut, such as from a steam cracking process or a fluid catalytic cracking process, primarily for conversion of $C_4$ and $C_5$ olefins to propylene via metathesis.

In typical olefin plants, there is a front-end demethanizer for the removal of methane and hydrogen followed by a deethanizer for the removal of ethane, ethylene, and $C_2$ acetylene. The bottoms from this deethanizer tower consist of a mixture of compounds ranging in carbon number from $C_3$ to $C_6$. This mixture is separated into different carbon numbers typically by fractionation.

The $C_3$ cut, primarily propylene, is removed as product and is ultimately used for the production of polypropylene. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut consisting of $C_4$ acetylenes, butadiene, iso and normal butenes, and iso and normal butane can be processed in many ways. A typical steam cracker $C_4$ cut contains:

| | |
|---|---|
| $C_4$ acetylenes | trace |
| Butadiene | 33% |
| 1-butene | 15% |
| 2-butene | 9% |
| Isobutene | 30% |
| Iso & Normal butane | 13% |

The $C_4$ acetylenes are first removed by selective hydrogenation followed by butadiene extraction. Alternately they are hydrogenated along with butadiene to form butenes. Isobutene can be removed by fractionation, by reaction to methyl tertiary butyl ethylene using methanol, or by reaction with itself and normal butenes in a catalytic $C_4$ dimerization unit. The isobutene is typically removed before metathesis with ethylene since it is known to cause catalyst fouling when present in both concentrations greater than 10%. The $C_5$ and heavier stream is typically used in the production of gasoline but sometimes the $C_5$'s are separated and recycled to the cracking heaters.

The bottoms containing primarily the 1-butene and 2-butene are mixed with ethylene and passed through the metathesis or olefin conversion reacting step. In this conversion reaction step, the primary reaction is:

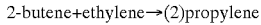

2-butene+ethylene→(2)propylene

The catalyst for this reaction is typically an oxide of Group VI A or Group VII A metals supported on either alumina or silica supports. In some cases, this oxide is admixed with a double bond isomerization catalyst such as MgO. In the reactor, the 2-butene and ethylene are metathesised to propylene. The 1-butene does not react with ethylene. The isomerization catalytic activity incorporated allows 1-butene to be isomerized to 2-butene which is then reacted with the ethylene. The effluent containing propylene, unreacted ethylene and butenes and some $C_5$ and heavier products is first passed through a deethylenizer for removal of that unreacted ethylene and then to a depropylenizer where product propylene is removed overhead. The bottoms may be sent to a debutanizer where unreacted $C_4$s are recovered and recycled. The $C_5$ and heavier fraction is typically sent to gasoline. Alternately, a $C_4$ stream is withdrawn from the depropyleneizer above the bottoms and recycled with the net bottoms of $C_5$ and heavier again being sent to gasoline.

In the conventional process such as generally described above, there are several problems or disadvantages. First, there are separate fixed bed hydrogenation units for the $C_3$'s and butadiene. In the butadiene hydrogenation step, if high 2-butene concentrations are desired, additional hydrogenation is specified in order to maximize the hydroisomerization of 1-butene to 2-butene. In the hydroisomerization of 1-butene to 2-butene in the selective butadiene hydrogenation unit, there is a substantial loss (10+%) of butenes to paraffins which represents a considerable feed loss to the conversion step. Further, if fractionation is employed for the isobutene removal step, there is an additional loss of butenes since 1-butene is difficult to separate from isobutene without a very expensive fractionation tower. There typically is a 60% conversion of $C_4$'s to propylene in the metathesis step. If there is a side draw of $C_4$'s from the depropylenizer for $C_4$ recycle, there can be a buildup of $C_5$ and heavier compounds due to the limitations on purity which needlessly load the conversion reactor. In addition, the $C_4$'s that are recycled have a high concentration of 1-butene due to the isomerization reaction within the metathesis bed.

SUMMARY OF THE INVENTION

The object of the present invention is to provide an improved process for the conversion of olefins to maximize the production of propylene from a $C_3$ to $C_6$ cut from a steam or other cracking process. The invention involves the replacement of some separate hydrogenation steps with catalytic distillation hydrogenation operating along with an olefin conversion reaction to provide the maximum isomerization of 1-butene to 2-butene and the maximum metathesis of 2-butene and ethylene to propylene.

DESCRIPTION OF THE PREFERRED EMBODIMENT

Figure 1:
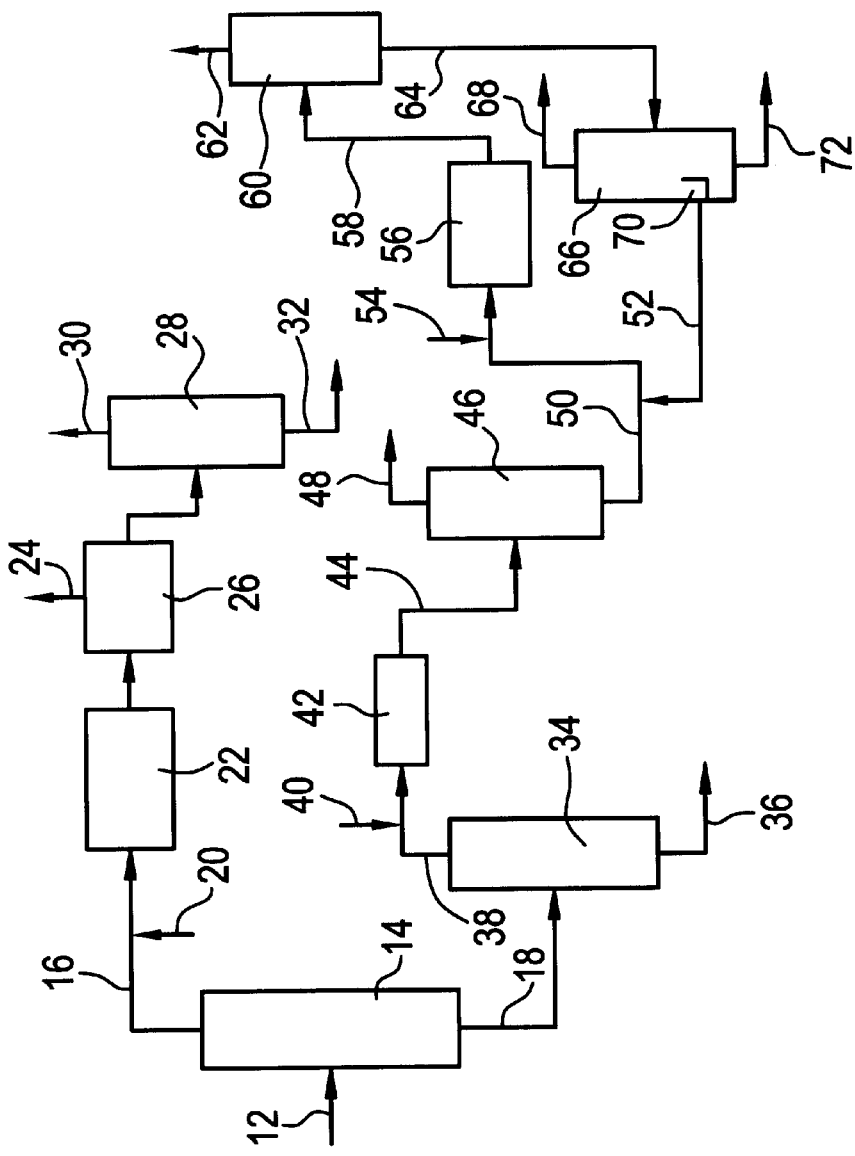
FIG. 1 is a flow diagram of the prior art process for treating a $C_3$ to $C_6$ cut from a steam cracking process for the production of propylene.

First, before describing the process of the present invention, the prior art process for separating a steam or catalytic cracker $C_3$ to $C_6$ cut and processing the $C_4$'s through an olefin conversion process as depicted in FIG. 1 will be described. The feed 12 is a $C_3$ to $C_6$ mixture from the deethanizer bottoms of a steam cracking process. This feed 12 contains primarily propane, propylene, butane, 1-butene, 2-butene, isobutene, butadiene and acetylenic hydrocarbons as well as various $C_5$ and $C_6$ components. The feed 12 is fed to the depropanizer column 14 where the $C_3$ components are removed overhead at 16 and the bottoms 18 are the $C_4$ and heavier components. Hydrogen 20 is injected into the overhead 16 and the $C_3$ acetylenes and dienes (methylacetylene and propadiene) are hydrogenated in fixed bed reactor 22 primarily to propylene. Excess hydrogen 24 is stripped at 26 and the $C_3$'s are fractionated in column 28 to recover the propylene overhead 30 and the propane bottoms 32.

The $C_4$ and heavier bottoms 18 from the depropanizer 14 are fed to the debutanizer column 34 where the $C_5$ and heavier ($C_6$) components are removed as bottoms 36. The remaining overhead 38 now contains primarily butane, 1-butene, 2-butene, isobutene and butadiene. Overhead 38 is injected with hydrogen and then passed to the selective hydrogenation unit 42 for hydrogenation of the butadiene and the hydroisomerization of the 1-butene formed from butadiene to 2-butene.

In this hydrogenation/hydroisomerization at 42, there is typically a loss of more than 10% of the butenes to butane if the effluent 44 is processed to have a desired mole ratio of 2-butene to 1-butene of about 8 or higher. The effluent 44 is then fed to the de-isobutylene column 46 where isobutylene is removed overhead at 48. There is also a fractionation loss of 1-butene with the isobutylene since 1-butene has a similar volatility. Alternately, reactor 42 could be operated to have less loss of butenes but the bottoms will then have a higher 1-butene concentration. In another alternate, stream 44 could be sent to a methyl tertiary butyl ethylene (MTBE) unit and the isobutylene removed via reaction with methanol.

The bottoms 50 now containing primarily 2-butene or a mix of 2-butene and 1-butene are mixed with a recycle $C_4$ stream 52 and an ethylene stream 54 and fed to the olefin conversion reactor 56 containing a conventional metathesis catalyst. In the reactor 56, the primary reaction is:

2-butene+ethylene→(2)propylene

1-Butene will not react with ethylene. However 1-butene can undergo the following reactions:

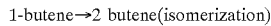
1-butene→2 butene(isomerization)

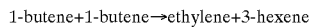
1-butene+1-butene→ethylene+3-hexene

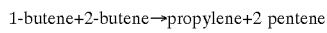
1-butene+2-butene→propylene+2 pentene

The conventional metathesis is a reaction between ethylene and 2-butene to form two propylene molecules. The catalyst system used is typically a mixture of an isomerization catalyst (MgO) and a metathesis catalyst ($WO_3$ on silica).

It is important to note that 1-butene will not react with ethylene since new molecules will not be formed when the double bonds shift. It forms ethylene and 1-butene again. The only way 1-butene can react with ethylene is to isomerize to 2-butene and then react with the ethylene to form propylene. As shown above, 1-butene can react with itself (slowly) to form ethylene and 3-hexane. It is slow since only one of two possible stereo positions will form new molecules when they shift. The alternate stereo position will simply reform two individual 1-butenes. This is referred to as a "half-productive" reaction. Importantly, 1-butene can also react with 2-butene to form propylene and 2-pentene. Since only one propylene is formed from two butene molecules, this is not as selective as the reaction with ethylene. Still further, the presence of high concentrations of 1-butene has shown to have a negative impact on the metathesis catalyst life due to fouling in those cases where the reaction involves ethylene and 2-butene. The product pentenes and hexenes formed in the non-selective reactions continue to react to form still heavier molecules eventually fouling the catalyst. Thus in the conventional prior art process, if the loss of butenes in the fractionation step is minimized by minimizing the isomerization of 1-butene to 2-butene, catalyst fouling in the reactor becomes a problem.

The effluent 58 from the reactor 56 is fed to the deethylenizer 60 where excess ethylene is removed overhead at 62. The bottoms 64 from the deethylenizer 60 now containing propylene, some unconverted 1-butene and 2-butene, butane and some small quantity of $C_5$ and heavier components are fed to the depropylenizer 66 where product propylene is removed overhead at 68. There is usually a side draw 70 of $C_4$'s which provides the recycle to the olefin conversion reactor 56. The $C_4$'s at this point are a mix of 2-butene and 1-butene. The unreacted $C_4$'s have a high concentration of 1-butene since the conversion of 1-butene is lower than the conversion of 2-butene. This is a result of the fact that 1-butene conversion must be a two-step process (first to 2-butene and then react with ethylene to form propylene). Recycle of this $C_4$ stream results in a net increase in the 1-butene concentration of the feed to the metathesis reactor.

With time on stream, the ratio of 2-butene to 1-butene in the effluent decreases even further as the isomerization activity is lost. This means that any recycle of unconverted $C_4$'s has an increasingly high 1-butene concentration leading to a still lower 2-butene to 1-butene ratio with time in the feed to the reactor 56. The bottoms 72 from the depropylenizer 66 now contain some $C_4$'s and most of any remaining heavier components. However, with the $C_4$ side draw for recycle, there is a buildup of $C_5$ components which needlessly loads the olefin conversion reactor 56. Although a separate tower could be employed for $C_5$ removal, that would require significant additional capital expense.

In the conventional system described, the overhead from the debutanizer is hydrogenated to turn the $C_4$ acetylenes and butadiene into butenes. Depending upon the conditions, butadiene will form varying mixtures of 1-butene and 2-butene. The product of this hydrogenation is primarily 1-butene. With excess hydrogen, there is some hydroisomerization and 1-butene is turned into 2-butene. Unfortunately with excess hydrogenation some butenes are turned into butanes and these represent a loss of feedstock for the metathesis reactions since they cannot react. For example, to obtain a desired 2-butene to 1-butene product ratio of 10/1, there is 11.7% conversion of butenes to butanes. Loss of butenes in this case assumes all butadiene goes to butenes. Thus 11.7% of the butadiene plus butenes in the feed go to butane. This is a major loss of butene. This loss can be minimized by using less hydrogen but the product will then have an undesirable 2-butene to 1-butene ratio lower than 10, maybe 5 or less. In essence, the higher the 2-butene product from the hydrogenation step, the lower the total quantity of butenes. This is an economic tradeoff since the 1-butenes will react with 2-butenes and reduce metathesis reaction selectivity as described above.

The higher quantity of 1-butenes from the hydrogenation step presents a second problem. As mentioned, isobutylene should be removed from the feed to the metathesis unit to less than 10%. Since 1-butene has a boiling point close to isobutene, if fractionation is used to separate isobutylene, some 1-butene will be lost with the isobutylene overhead. This is an additional loss of feed butenes to the metathesis step.

Figure 2:
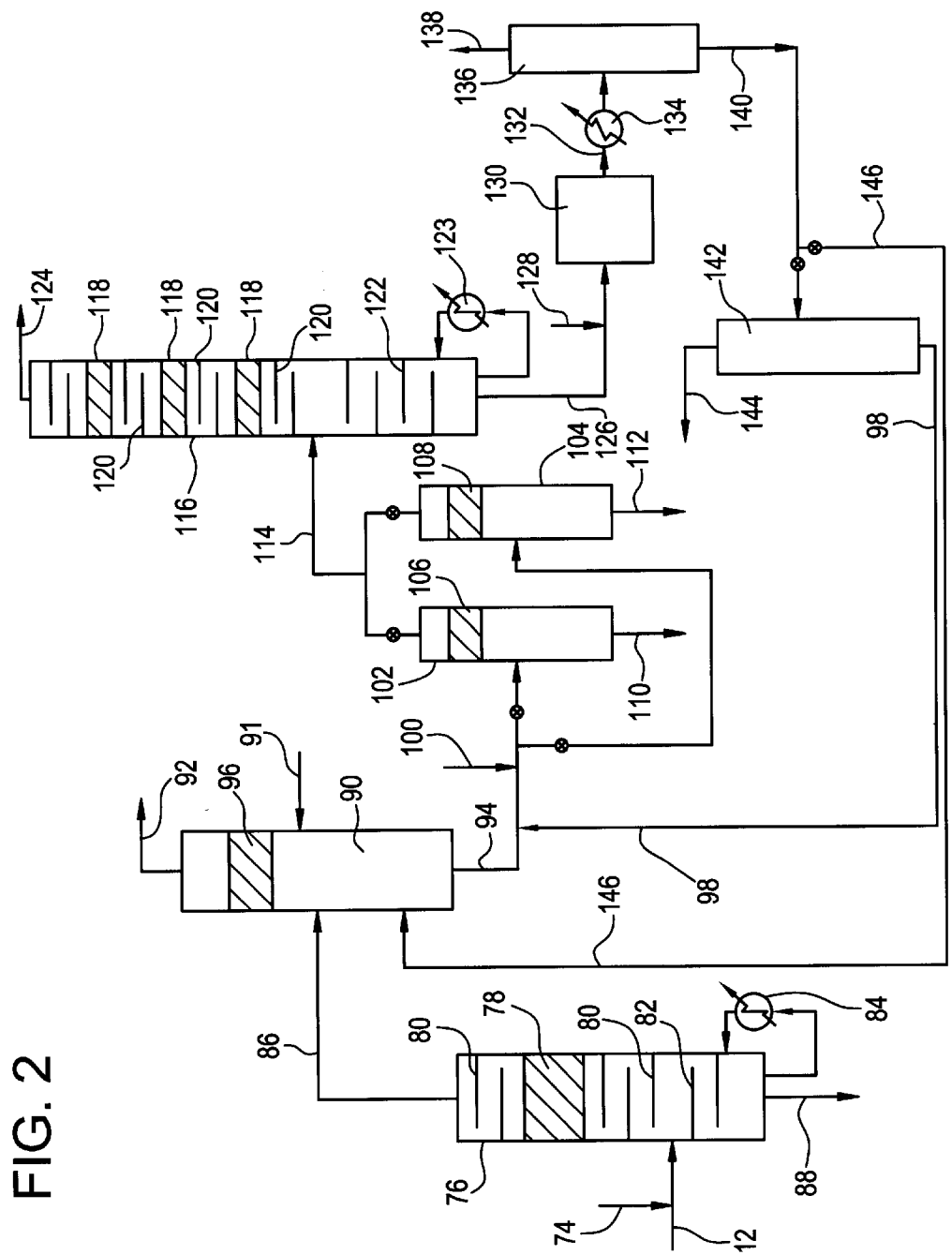
FIG. 2 is a flow diagram of a process according to the present invention for treating the same cut for improved propylene production.

The preferred embodiment of the present invention, which is an improvement on the prior art process just described, is illustrated in FIG. 2. In this improved process, the feed 12 is mixed with hydrogen 74 and fed to a catalytic distillation column 76 containing at least one hydrogenation catalyst bed 78 and distillation internals 80 in the rectifying/reaction section, additional distillation internals 82 in the stripping section below the feed and a reboiler 84. The distillation internals may be of any desired type such as conventional trays or packing. The catalyst in the catalytic distillation packing may, for example, be a palladium-based hydrogenation catalyst. This column 76 is operated as a debutanizer although it can also be operated as a depentanizer and it is operated for substantial hydrogenation of the acetylenic and diene components with no hydrogenation losses of butenes and propylene. Hydrogen is typically added at a level representing from 1.0 to 1.5 times the hydrogen that is required to hydrogenate the dienes and acetylenes to olefins. This is typically less than the quantity of hydrogen used in fixed bed reactors. The column is operated at a temperature and pressure consistent with the fractionation conditions. If the column is a debutanizer, then typically the pressure is on the order of 130–170 psig with a temperature of 190° F. If the column is a depentanizer, then the pressure is similar but the temperatures are higher (210–220° F.). These conditions are variable depending upon the column design. These temperatures and pressures are preferred to balance the rate of reaction which is sensitive to temperature and pressure, the desired selectivity with lower temperatures being preferred, and the desire to minimize the use of refrigeration for condensing duty on the column overhead. Catalytic distillation allows the matching of concentration of reactive components in the column and control of temperature by changing pressures to allow for maximum selectivity. The column is operated such that in the net overhead, there is only a slight excess quantity of acetylenes and dienes, on the order of <1000 ppm. Under these conditions, the loss of olefins to paraffins will be minimized. The remaining acetylenics and dienes are then reacted fully later under even lower hydrogen concentrations to keep losses low. Essentially all of the methyl acetylene, propadiene, vinyl acetylene, ethyl acetylene and butadiene are hydrogenated to their respective olefins.

The overhead 86 from the column 76, which is illustrated as a debutanizer, contains propane, propylene, butene-1, butene-2, isobutylene and some of the $C_5$ components. The bottoms 88 basically contain the remaining $C_5$ and the heavier components which are further processed as desired. The overhead 86 is fed to a de-propanizer tower where the propane and propylene are removed overhead at 92 and sent for separation and recovery of propane and propylene. The excess hydrogen in stream 86 is removed in the vents from the overhead condensers on tower 76. The bottoms 94 contain the $C_4$ and heavier components including the butenes. This tower 90 may contain a catalyst bed 96 which is termed a "guard bed" which functions to hydrogenate any residual methyl acetylene and propadiene which may have been carried over from tower 76. As mentioned above, slight amounts of hydrogen are added to column 90 via stream 91 to allow for this reaction. For the most part, the hydrogen absorbed in the liquid overhead from column 76 is sufficient but low levels of hydrogen can be added if needed.

The bottoms 94 from column 90 are $C_4$'s if column 76 is a debutanizer or a mix of $C_4$ and $C_5$ if column 76 is a depentanizer. The stream 94 is mixed with a recycle $C_4$ stream 98, which contains $C_4$ components such as 1-butene and 2-butene as well as some $C_5$ components, and further mixed with a small amount of hydrogen 100. This mixed stream is fed to one of the two columns 102 and 104 which are in parallel and operated alternately for catalyst regeneration or replacement. The catalyst beds 106 and 108, which are also termed "guard beds", serve to hydrogenate any residual butadiene which may have broken through in the overhead from column 76 to keep the selectivity high. The low level of hydrogen and a lower activity palladium catalyst is selective for hydrogenating only the acetylenes and dienes.

The bottoms 110 and 112 from the columns 102 and 104 contains any residual $C_5$ and heavier components present in the recycle stream 98 or C5's in the net feed 94 if tower 76 is operated as a depentanizer. This will prevent their return to the process and define the $C_5$ content in the ultimate feed to the metathesis unit which will increase catalyst on stream time.

The ability to do the bulk of the hydrogenation in column 76 and cleanup in columns 90 and 102/104 using very controlled amounts of hydrogen keeps selectivity of butadiene to butenes high and avoids losses to butanes. This is an advantage of the catalytic distillation of the present invention. Separate reactor systems are not being added with separate hydrogen control but instead taking place in columns already required for fractionation. This approach both improves selectivity and saves equipment compared to splitting the hydrogen in separate fixed bed reactor systems and maximizes the butene flow to the metathesis reaction step thus maximizing propylene.

The overhead 114 from the columns 102 and 104 is the $C_4$ components and is primarily a mixture of isobutylene, 1-butene and 2-butene. This mixture 114 is fed to the catalytic fractionation column 116 which has catalyst beds 118 located above the feed 14 in the rectifying section alternating with distillation trays 120 or distillation packing. Distillation trays 122 or equivalent distillation packing are also located in the stripping section of this column 116 and the column has a reboiler 123. Column 116 is the hydroisomerization tower and the deisobutylenizer. The catalyst used is a palladium catalyst on a support such as alumina. The hydrogen added is on the order of 0.01 to 0.1 mols hydrogen per mol of butenes. The hydrogen is added upstream of columns 102 and 104 and will first hydrogenate the butadiene. Any remaining hydrogen will act as a co-feed for the hydroisomerization. The intent is not to hydrogenate any further so the least amount of hydrogen required is chosen. The exact quantity will depend upon the amount of butadiene that is carried over and the exact choice of catalyst in columns 102 and 104 and in column 116. Operating temperatures are on the order of 100–150° F. The advantages of column 116 is that 1-butene is isomerized to 2-butene almost completely. By reacting 1-butene to 2-butene, the losses of 1-butene overhead are minimized and the butene feed tot he metathesis reactor is maximized. Also, passing the recycle $C_4$'s through columns 102/104 and column 116 changes the ratio of 2-butene to 1-butene in the recycle and thus high 1-butene concentration in the metathesis reactor feed is eliminated. There is almost a constant essentially pure 2-butene feed sent to the olefin conversion reactor which maximizes selectivity and catalyst onstream time.

One of the functions of the column 116 is to remove the isobutylene overhead at 124 with the isobutene having a low 1-butene content. The 1-butene boils at a lower temperature than the 2-butene and thus will tend to rise in the fractionation column 116. The isobutylene is the lowest boiling of the mixture and will tend to go overhead. The 2-butene is fractionated from the mixture and is removed as the bottom product 126. As the 1-butene rises through the rectifying section in contact with the hydrogenation catalyst beds 118 and in the presence of the extremely low quantities of hydrogen, the 1-butene is isomerized to 2-butene which then moves down the column. Moving up in the column, the distillation fractionation of the 1-butene increases due to volatility but it is subsequently isomerized to 2-butene. The equilibrium driving force for the isomerization of the 1-butene increases as the 1-butene concentration increases by fractionation and the product 2-butene is continually removed from the equilibrium zone as it moves toward the bottom of the tower. The net result is that the 1-butene is hydroisomerized almost to extinction. This isomerization of 1-butene to 2-butene is important in order to limit the non-selective reactions of 1-butene with itself or 2-butene in the olefin conversion reactor to produce pentenes and hexenes rather than the desired production of propylene.

The bottom product 126 from the column 116 is essentially pure 2-butene. This is admixed with ethylene 128 and fed to the olefin conversion reactor 130 containing a catalyst for carrying out the metathesis reaction such as $WO_3$ supported on silica, molybdenum oxide on alumina, or rhenium oxide on alumina. The reaction is as follows:

ethylene    2-butene    propylene

In addition, however, there is the following side isomerization reaction particularly if the catalyst includes an isomerization component:

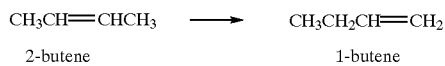
2-butene    1-butene

This side reaction occurs to some extent over the metathesis catalyst itself and to a greater extent if there is a specific isomerization catalyst (ca MgO) admixed with the catalyst. The 1-butene and 2-butene then immediately react as follows:

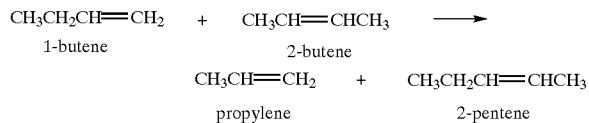
1-butene    2-butene
propylene    2-pentene

The extent of side reactions will depend upon the isomerization character of the catalyst. MgO is an isomerization catalyst and the alumina supports of the other catalysts have significant isomerization activity. In the conventional system, where appreciable quantities of 1-butene are present in the feed either from operation at low 2-butene/1-butene ratios in the hydrogenation step or by recycle of stream 98, it is desirable to have a high isomerization catalyst activity to push any 1-butene toward 2-butene and thus react with the excess ethylene to form propylene. Further, high excess amounts of ethylene are used in the conventional system to minimize the reaction of 1-butene with 2-butene. This is an economic penalty due to higher separation costs associated with removing ethylene from the reaction products.

In the system of the present invention however, with an essentially pure 2-butene stream entering the reactor, a lower amount of isomerization activity is desired. This will allow operation at lower ethylene to butene ratios than possible with systems with high 1-butene concentrations and thus realize economic advantage.

In accordance with one aspect of the present invention, butene-2 and ethylene are subjected to a metathesis reaction under conditions and in the presence of a metathesis catalyst that minimizes or eliminates double bond isomerization to produce a reaction product that has a high selectivity to propylene. Specifically, the catalyst and reaction conditions are such as to minimize isomerization of the butene-2 starting material to butene-1. This will allow for operation at the lowest ethylene/butenes ratio at maximum selectivity.

The catalyst used in this aspect for the metathesis reaction may be a supported or unsupported catalyst and the overall catalyst is one that has a minimized amount of both acidic and basic sites. A catalyst that has a reduced amount of both acidic and basic sites (preferably essentially no acidic and basic sites) improves the selectivity of the metathesis of the butene-2 with ethylene to form propylene. If a support is used, such support has a minimized amount of both acidic and basic sites and preferably essentially no acid and essentially no basic sites. Preferred supports are silica or zirconia oxide. Alumina is a support that is known to have higher acidity and thus is not preferred. The catalyst may also include a promoter to reduce acidity; for example, an alkali metal (sodium, potassium or lithium), cesium, a rare earth, etc.

In one embodiment, the catalyst or catalyst mixture contains essentially no magnesium oxide in that magnesium oxide catalyst promotes isomerization. Thus, for example, a preferred catalyst (supported or not supported) is tungsten oxide, molybdenum oxide, or rhenium oxide, with tungsten oxide being particularly preferred.

The degree of isomerization activity of the catalyst can be measured by the extent of reaction of a pure butene-2 stream passed over the catalyst at 300 C and a WHSV of 15. Catalysts with low isomerization activity will have conversions of 2-butene of less than 10%. Generally, reaction conditions that tend to favor the primary reaction and discourage subsequent reactions are preferred. Thus a lower pressure and shorter residence times tend to minimize the isomerization reaction.

The effluent 132 from the reactor 130 is cooled at 134 and fed to fractionation column 136 where any remaining excess ethylene is removed overhead at 138 for recycle in the process. The bottoms 140 are a mix of the propylene and $C_4$ and $C_5$ components and possibly some even heavier side reaction products. These bottoms 140 are fed to the depropylenizer column 142 where the final propylene product 144 is fractionated overhead. The entire bottoms 98 from the depropylenizer 142 are recycled to the columns 102 and 104 for the removal of the $C_5$'s and heavier and reprocessing of the $C_4$'s through the deisobuteneizer 116. Since there is some 2-butene isomerized to 1-butene in the metathesis reactor 130, the unconverted $C_4$'s from the depropylenizer 142 in stream 98 contain both 1-butene and 2-butene. By recycling this stream 98, 2-butene is selectively fed to the metathesis reactor 130 thereby increasing the cycle time onstream and the selectivity to propylene. This recycle of the entire bottoms 98 to the bottoming columns 102 and 104 as compared to the side draw 52 in the prior art of FIG. 1 results in the withdrawal of the $C_5$'s from the process so that a pure 2-butene stream is maintained as the feed to the metathesis reactor 130. This also increases the cycle life and improves overall reaction selectivity.

An option to the process of the present invention is when isobutylene is removed via a means other than fractionation such as via reaction with methanol to form MTBE. The butenes stream would then contain only butenes and butane with small quantities of isobutylene. In that case, column 116 would operate with minimum flow overhead (stream 124) in a condition of near total reflux. The column would primarily be a hydroisomerization tower rather than a combination hydroisomerization tower/deisobutyleneizer.

Another option to the process of the present invention is that all of the bottoms 140 from the deethylenizer column 136 can be recycled at 146 to the depropanizer column 90 thereby eliminating the depropylenizer column 142. In this variation, all of the propylene is recovered in the overhead 92 from the column 90 along with the propane. The propylene is then separated from the propane.

Another variation is that column 76 can be operated as a depentanizer in which case the $C_5$'s as well as the $C_4$'s and lighter components pass overhead. The acetylenic and diene C$_5$'s are hydrogenated in the column 76 and now all of the C$_5$'s flow out the bottom of columns 102 and 104.

In the present invention, the catalytic hydrogenation distillation column 76 has a high selectivity in the hydrogenation of butadiene to form butenes with a low loss to the formation of butanes. The provision of the two columns 102 and 104 enables the catalyst in one column to be regenerated while the other column remains on stream. This assures that the butadiene level can be kept within the limits needed for the olefin conversion reaction. Another significant feature of the invention is that the 1-butene is converted to 2-butenes and that only the 2-butene is fed to the olefin conversion reaction together with the injected ethylene thereby increasing selectivity for propylene and increasing the life of the catalyst.

EXAMPLE 1

In this example, identical C$_3$ to C$_6$ cracking heater product streams are processed to form a C$_4$ feed to the olefins conversion or metathesis unit using prior art technology and alternately catalytic distillation technology. The material balances are developed without considering recycle of the unconverted butenes from the olefins conversion reaction section.

In the conventional case, 414955 lb/hr of condensate stripper and de-ethanizer bottoms feed is sent to a depropanizer column along with some vents from separation drums in the cracked gas compression train. The overhead from this tower is 164,382 lb/hr containing 10,572 lb/hr methyl acetylene and propadiene and 147083 lb/hr propylene. Hydrogen is added at a 1.2 molar ratio to MAPD and the mix sent to a fixed bed hydrogenation unit where 77% of the MAPD is converted to propylene and the balance to propane. The bottoms from this tower is sent to a debutanizer where 125,181 lb/hr of C$_4$'s pass overhead and the balance (210,214 lb/hr including the vent streams) passes out the bottom. The following table shows the mass flow of C$_4$ compounds in lbs./hr. to and from the fixed bed hydrogenation reactor:

|              | To Reactor | From Reactor |
|--------------|------------|--------------|
| 1,3 butadiene | 41966      | nil          |
| 1-butene      | 19100      | 5719         |
| 2-butene      | 11219      | 59335        |
| isobutylene   | 38125      | 36568        |
| n-butane      | 11137      | 20070        |
| i-butane      | 3595       | 5003         |
| Total         | 125172     | 126665       |

This mixture then passes through a selective hydrogenation step to hydrogenate the butadiene to butenes as well as hydroisomerize the 1-butene to 2-butene. This adds 1493 lb/hr hydrogen. As can be seen, there is a net gain of 10355 lb/hr of paraffins resulting from the oversaturation of the butene/butadiene stream. The ratio of 2-butene to 1-butene increases from 0.58 in the feed to 10.37 in the effluent. Note that if lower amounts of hydrogen were used, there would be less olefin loss to paraffins but the ratio of 2-butene to 1-butene would be lower. In this case, the loss of n-olefins critical for olefins conversion feedstock is 7168 lb/hr or 9.9%. Importantly, when the isobutylene is removed via fractionation, some of the 1-butene goes with it. After fractionation the net n-butenes feed to the olefins conversion reaction section is even lower. The net n-butenes to the reactor are 58,326 lb/hr. In addition there is 18252 lb/hr of n-butane which represents 23.6 wt % of the feed.

As an alternate, the identical feed is fed to a debutanizer in the process of the invention. In addition, 4600 lb/hr of hydrogen is added to the feed. The overhead of the tower contains both the C$_3$ and C$_4$ fractions and is 289580 lb/hr. The catalyst beds in the debutanizer have converted 85% of the methylacetylene and propadiene and 96% of the butadiene. The overhead is then sent to a depropanizer tower where there are catalyst beds located in order to complete the hydrogenation of the MAPD to propylene and propane and the butadiene to butenes. On a basis similar to the conventional case, the C$_4$ stream components in the feed 12 to column 76 and the bottoms 94 from the depropanizer are as follows:

|              | Feed 12 | Bottoms 94 |
|--------------|---------|------------|
| 1,3 butadiene | 41966   | nil        |
| 1-butene      | 19100   | 17918      |
| 2-butene      | 11219   | 51358      |
| isobutylene   | 38125   | 36092      |
| n-butane      | 11137   | 15695      |
| i-butane      | 3595    | 3591       |
| Total         | 125172  | 124654     |

The lower total reflects some additional fractionation losses. The bottoms is then sent to a deisobutylenizer where the isobutylene is removed and the 1-butene is hydroisomerized in a multiple catalyst beds located within the fractionation section. Much of the feed 1-butene is converted to 2-butene and passes out of the bottom of the tower. The net feed to the olefins conversion reaction section contains 66337 lb/hr of n-butenes or 13% more feed than the conventional case. In addition there are 14301 lb/hr butanes in the feed or 17% of the feed.

By processing the C$_3$ to C$_6$ cut by the process of the invention, the net feed to the olefins conversion unit is increased by 13% thus increasing the yield of propylene. Further, since the butane concentration is lower, the equipment does not have to be designed for the higher flows and thus can be less expensive. In an integrated case where each system also included the recycle of the unreacted C$_4$ olefins from the olefins conversion unit, the differences would be greater.

EXAMPLE 2

In the prior art system, the unreacted C$_4$ olefins consist of a mixture of 1-butene and 2-butene. At the conditions within the reactor system, the hydroisomerization equilibrium is such that there is a 3/1 ratio of 2-butene to 1-butene. However, in the reactor, with the 2-butene reacting rapidly with ethylene and the 1-butene not reacting with ethylene, the reactor effluent in most cases has a 1-butene content that is above the predicted equilibrium value. As the catalyst system ages, the isomerization activity of 1-butene to 2-butene is the first to decay. This contributes even more to a gradual reduction in the 2-butene to 1-butene ratio and the increase in fouling of the catalyst. In order to examine this phenomena, a case was developed where an initial fresh feed was reacted and a simulated feed reacted assuming degradation of the 2-butene to 1-butene ratio occurred.

In a specific conventional case in a pilot plant test without considering recycle, a fresh feedstock with a 2-butene to 1-butene ratio of 5.23 was fed to a metathesis reaction system utilizing a catalyst consisting of a physical mixture of WO$_3$ on silica and MgO. In the initial operational period (20 hrs on stream) the conversion of 1-butene in the reactor was 64% and the conversion of the 2-butenes was 71.6%. In the effluent, the ratio of 2-butene to 1-butene was 3.96. If the product C$_4$ stream was admixed with the fresh feed and assuming an overall conversion of 90% (with recycle), the actual reactor feed would have had a 2-butene to 1-butene ratio of 4.56.

Over the next 400 hours, the isomerization activity of the catalyst decayed. A feedstock with a 2-butene to 1-butene ratio of 3.25 was used to represent the changing ratio with age. At 700 hours on stream, the product had a ratio of 2-butene to 1-butene of 1.30. Over that same time period, the 1-butene conversion had dropped to 38%. If the original fresh feed with a ratio of 5.23 was admixed with the recycle having a ratio of 1.30 at 38% 1-butene conversion, the resultant actual reactor feed butene ratio would have been 2.25. Thus over the 700 hours, in actual commercial operation, the ratio would have dropped from 4.56 to 2.25. This resulted in accelerated fouling of the catalyst and the selectivity to propylene dropped from an initial 98.86 to 93.4%. In the system of the invention, since the recycle feed passes back through the hydroisomerization catalytic distillation system, there would be no such degradation and a high level of performance could be maintained over the life of the catalyst.

Example of Low Isomerization

A pure (99%) 2-butene stream was passed over a WO$_3$ on silica catalyst at a temperature of 599 F., a pressure of 275 psig and a WHSV of 16. The resultant conversion of the 2-butene was 7.3%. The product selectivities were 48.2% to propylene and 46.2% to 2-pentene and 3.8% to C$_7$ plus. This indicates that essentially 3.6% of the 2-butene was isomerized to 1 butene which reacted with the excess 2-butene to form propylene and 2-pentene. The net isomerization is low.

In a second test, the same 2-butene stream was passed over a catalyst consisting of the same WO$_3$ on silica but admixed with MgO. The MgO is a known isomerization catalyst. The temperature was 640 F. and the space velocity was 21. The operating pressure was 275 psig. Under these conditions, the conversion was 40%. The selectivity to propylene was 45% and the selectivity to 2 pentene was 39%. The higher conversion indicates a much greater isomerization of 2-butene to 1-butene and reaction to form propylene and 2-pentene. The effluent unconverted C$_4$ stream had a ratio of 2-butene to 1-butene of 3.6 indicating a substantial conversion of the 2-butene to 1-butene. This would have a very negative effect on net feed composition as referenced in example 2.

What is claimed is:

1. A process for the preferential conversion to propylene of a C$_3$ to C$_6$ cut containing propylene, butane, 1-butene, 2-butene, isobutene and acetylenic and diene components including butadiene comprising the steps of:
   (a) simultaneously fractionating and selectively hydrogenating said cut in the presence of an hydrogenation catalyst whereby said acetylenic and diene components including said butadiene are hydrogenated and said C$_3$ and C$_4$ and some of said C$_5$ components are fractionated overhead;
   (b) separating said C$_3$ and some C$_5$ components in said overhead from said C$_4$ components comprising a mixture of isobutene, 1-butene and 2-butene;
   (c) simultaneously fractionating and hydrogenating and hydroisomerizing said C$_4$ components in the presence of an hydrogenating catalyst whereby said 1-butene is isomerized to 2-butene and whereby any remaining butadiene is hydrogenated and isobutene is separated overhead and 2-butene is separated as bottoms;
   (d) injecting said 2-butene bottoms with ethylene and reacting said 2-butene and ethylene in the presence of a metathesis catalyst whereby a metathesis product containing propylene is formed.

2. A process as recited in claim 1, wherein said metathesis product further contains excess ethylene and C$_4$ and C$_5$ components and further including the steps of separating in a depropylenizer said excess ethylene and said C$_4$ and C$_5$ components from said propylene in said metathesis product and recycling said C$_4$ and C$_5$ components to step b for the separation of said C$_5$ components and for the further processing of said C$_4$ components in step c.

3. A process as recited in claim 2 wherein said hydrogenating catalyst in steps (a) and (c) is Pd.

4. A process as recited in claim 2 wherein said C$_3$ components include methyl acetylene and propadiene and said step (b) consists of processing in a depropanizer having a catalyst in a rectifying section whereby methyl acetylene and propadiene are hydrogenated followed by processing in a debutanizer having a catalyst in a rectifying section whereby butadiene is hydrogenated.

5. A process as recited in claim 2 wherein said metathesis catalyst comprises tungsten oxide.

6. A process as recited in claim 2 wherein said metathesis catalyst comprises tungsten oxide supported on silica.

7. A process as recited in claim 4 wherein said recycled C$_4$ and C$_5$ components comprise a side draw from said depropylenizer.

8. A process as recited in claim 4 wherein said recycled C$_4$ and C$_5$ components comprise the bottoms from said depropylenizer.

9. A process as recited in claim 1 wherein said ethylene is separated from said metathesis product and including recycling the remaining metathesis product to step (b) for separation of propylene.

* * * * *